United States Patent
Peng et al.

(10) Patent No.: US 11,238,591 B1
(45) Date of Patent: Feb. 1, 2022

(54) MEDICAL IMAGE PROCESSING SYSTEM AND METHOD THEREOF

(71) Applicants: Taipei Medical University (TMU), Taipei (TW); Kaohsiung Chang Gung Memorial Hospital, Kaohsiung (TW)

(72) Inventors: Syu-Jyun Peng, Hsinchu County (TW); Fu-Yuan Shih, Kaohsiung (TW)

(73) Assignees: Taipei Medical University (TMU), Taipei (TW); Kaohsiung Chang Gung Memorial Hospital, Kaohsiung (TW)

(*) Notice: Subject to any disclaimer, the term of this patent is extended or adjusted under 35 U.S.C. 154(b) by 58 days.

(21) Appl. No.: 16/929,117

(22) Filed: Jul. 15, 2020

(51) Int. Cl.
- *G06K 9/00* (2006.01)
- *G06T 7/00* (2017.01)
- *A61B 90/00* (2016.01)
- *G16H 30/20* (2018.01)

(52) U.S. Cl.
CPC ............ *G06T 7/0014* (2013.01); *A61B 90/37* (2016.02); *A61B 90/39* (2016.02); *G16H 30/20* (2018.01); *A61B 2090/374* (2016.02); *A61B 2090/3983* (2016.02); *G06T 2207/10088* (2013.01);
(Continued)

(58) Field of Classification Search
CPC ......... G06T 7/0014; G06T 2207/10088; G06T 2207/20128; G06T 2207/30016; G16H 30/20; A61B 90/37; A61B 90/39; A61B 2090/3983; A61B 2090/374
See application file for complete search history.

(56) References Cited

U.S. PATENT DOCUMENTS

2013/0204114 A1* 8/2013 Huang ................ A61B 5/7282
600/409
2018/0117321 A1   5/2018 McIntyre et al.
(Continued)

FOREIGN PATENT DOCUMENTS

| CN | 102762253 A | 10/2012 |
|----|-------------|---------|
| CN | 101918855 B | 7/2013  |
| CN | 103917271 A | 7/2014  |

(Continued)

OTHER PUBLICATIONS

Andreas Horn et al., Probabilistic conversion of neurosurgical DBS electrode coordinates into MNI space(NeuroImage 150 p. 395-404, Feb. 3, 2017 DOI: 10.1016/j.neuroimage.2017.02.004 ).

*Primary Examiner* — Atiba O Fitzpatrick
(74) *Attorney, Agent, or Firm* — CKC & Partners Co., LLC

(57) ABSTRACT

A medical image processing system includes a memory and a processor coupled to each other. The processor accesses and executes instructions which memory stores to perform the following: obtaining a plurality of brain MR images corresponding to a subject, wherein the brain MR images corresponds to a subject brain space; accessing a DBS targets atlas corresponding to a specific stimulation area; transforming the DBS targets atlas from a MNI brain space to the subject brain space based on a DARTEL algorithm; marking at least one coordinate having a largest Voxel value in the brain MR images based on the transformed DBS targets atlas; and storing the brain MR images being targeted with the at least one coordinate into a predetermined format corresponding to a guiding device so that the guiding device displays the brain MR images being targeted with the at least one coordinate for guidance in DBS procedure.

10 Claims, 3 Drawing Sheets

(52) U.S. Cl.
CPC ............... *G06T 2207/20128* (2013.01); *G06T 2207/30016* (2013.01)

(56) References Cited

U.S. PATENT DOCUMENTS

2019/0126033 A1* 5/2019 Pradeep ............. A61N 1/36025
2021/0076972 A1* 3/2021 Novikov ............ G01R 33/4808

FOREIGN PATENT DOCUMENTS

| | | |
|---|---|---|
| CN | 102858406 B | 2/2015 |
| CN | 103077298 B | 9/2015 |
| CN | 102470247 B | 11/2015 |
| CN | 105030206 A | 11/2015 |
| CN | 106659412 A | 5/2017 |
| CN | 108537723 A | 9/2018 |
| CN | 108697402 A | 10/2018 |
| CN | 109414295 A | 3/2019 |
| CN | 109416937 A | 3/2019 |
| CN | 110461265 A | 11/2019 |
| TW | I442905 B | 7/2014 |
| TW | I586326 B | 6/2017 |
| TW | 201924607 A | 7/2019 |
| TW | 202101020 A | 1/2021 |

* cited by examiner

MEDICAL IMAGE PROCESSING SYSTEM AND METHOD THEREOF

BACKGROUND

Field of Invention

The disclosure relates to an electronic system and a method, and more particularly to an electronic system and a method for processing medical image to provide guidance functions.

Description of Related Art

Deep brain stimulation (DBS) uses an implantable pulse generator to import electrical current to the brain for electrical stimulation, and DBS has been proven to be used to treat many diseases. However, the accuracy of surgery has a considerable impact on the efficacy of DBS, and it can also influence the related complications of electrical stimulation of the surgery.

In response to this problem, in addition to recording with microelectrodes in the prior art, image guidance technology can be also used to help determine the stimulation point or confirm the electrode position during surgery. However, conventional image guidance systems may be difficult to determine the optimal stimulation location due to patient shake, magnetic resonance imaging issues, and poor electrophysiological signals.

SUMMARY

One aspect of the disclosure relates to a medical image processing system. The medical image processing system includes a memory and a processor. The processor is communicatively coupled to the memory. The memory stores at least one instruction. The processor stores and executes the at least one instruction to obtain a plurality of brain Magnetic Resonance (MR) images corresponding to a subject; access a deep brain stimulation (DBS) targets atlas corresponding to a specific stimulation area; transform the DBS targets atlas from a Montreal Neurological Institute (MNI) brain space to the subject brain space based on Diffeomorphic Anatomical Registration Through Exponential Lie (DARTEL) algorithm; mark at least one coordinate having a largest Voxel value in the specific stimulation area in the brain MR images basing on the DBS targets atlas being transformed; and store the brain MR images being marked the at least one coordinate into a predetermined format corresponding to a guiding device, so that the guiding device displays the brain MR images being targeted with the at least one coordinate for guidance in a DBS procedure.

Another aspect of the disclosure relates to medical image making method. The medical image making method includes obtaining a plurality of brain MR images corresponding to a subject, wherein the brain MR images correspond to a brain space of the subject; accessing a DBS targets atlas corresponding to a specific stimulation area; transforming the DBS targets atlas from a MNI brain space to the subject brain space based on DARTEL algorithm; marking at least one coordinate having a largest Voxel value in the specific stimulation area in the brain MR images basing on the DBS target atlas being transformed; and storing the brain MR images being marked the at least one coordinates into a predetermined format corresponding to a guiding device, so that the guiding device displays the brain MR images being targeted with the at least one coordinate for guidance.

These and other aspects of the present invention will become apparent from the following description of the preferred embodiment taken in conjunction with the following drawings, although variations and modifications therein may be effected without departing from the spirit and scope of the novel concepts of the disclosure.

It is to be understood that both the foregoing general description and the following detailed description are by examples, and are intended to provide further explanation of the invention as claimed.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment, and wherein.

DETAILED DESCRIPTION

Figure 1:
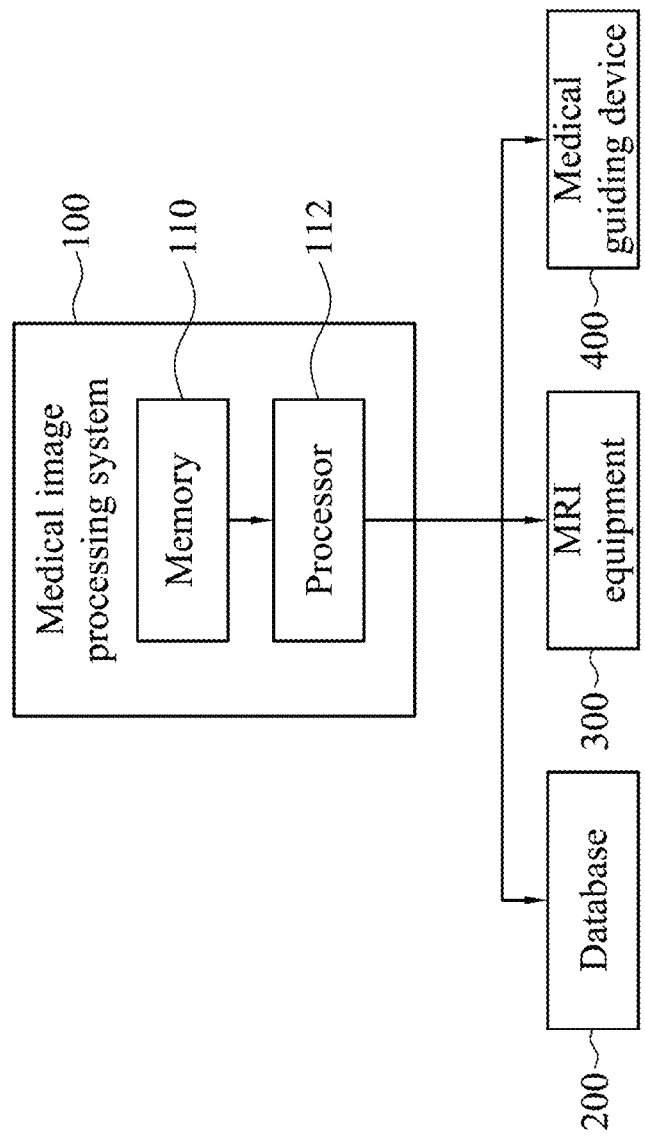
FIG. 1 schematically shows a schematic diagram of a medical image making system according to some embodiments of the present disclosure.

The present disclosure will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 schematically shows a schematic diagram of a medical image making system according to some embodiments of the present disclosure. As FIG. 1 shows, in some embodiments, a medical image making system 100 may include a memory 110 and a processor 112.

In some embodiments, the memory 110 can be Flash Memory, Hard Disk Drive (HDD), Solid State drive (SSD), Dynamic Random Access Memory (DRAM), or Static Random Access Memory (SRAM). In some embodiments, the memory 110 can store the instruction which is associated with a medical image making method.

In some embodiments, the processor 112 includes but not limited to a processor or an integration of many microprocessors, for example, Central Processing Unit (CPU) or Graphic Processing Unit (GPU). Since the processor (or microprocessor) is electrically coupled to a memory, the processor 112 can access the instruction from the memory 110, and execute specific application based on the instruction so as to implement aforementioned medical image making method. For facilitating the understanding of the medical image making method, detailed steps regarding the medical image making method are explained in the following paragraphs.

As FIG. 1 shows, in some embodiments, the processor 112 can be communicatively coupled to a database 200 in a selective manner. In some embodiments, the database 200 can store a plurality of Magnetic Resonance (MR) images, especially the MR images corresponding to at least one subject. In some embodiments, the database 200 can be implemented in a server external to the medical image making system 100. In some embodiments, the database 200 is also implemented in the memory 110.

As FIG. 1 shows, the processor 112 can be communicatively coupled to a piece of Magnetic Resonance Imaging (MRI) equipment 300 in a selective manner. In some embodiments, operations of the MRI equipment 300 generate a plurality of MR images, especially the MR images corresponding to at least one subject. In some embodiments, the MRI equipment 300 can store the MR images or send the MR images to a specific storage device for storing. In some embodiments, the MRI equipment 300 can be also replaced with other scan equipment which can obtain images of the inner structure of the brain.

As FIG. 1 shows, the processor 112 is further communicatively coupled to medical a guiding device 400 in a selective manner. In some embodiments, the medical guiding device 400 can provide (i.e., display) MR images with visualization, especially the MR images corresponding to at least one subject. In some embodiments, medical practitioners (i.e., doctors) would know which part of a body of a subject is treated during a treatment procedure with the medical guiding device 400, and this is useful especially in invasive treatment.

It should be understood that aforementioned "electrical coupling" or "communicatively coupling" can be referred to physically or non-physically coupling. For example, in some embodiments, the processor 112 can be coupled to the database 200 via physical circuit. In some embodiments, the processor 112 can be coupled to the MRI equipment 300 and the medical guiding device 400 with wireless communication protocols. However, the coupling method in the present disclosure is not limited to aforementioned embodiments. By the aforementioned coupling method, the processor 112 can transmit data with the database 200/the MRI equipment 300/the medical device 400 in unidirectional or bidirectional way.

Figure 2:
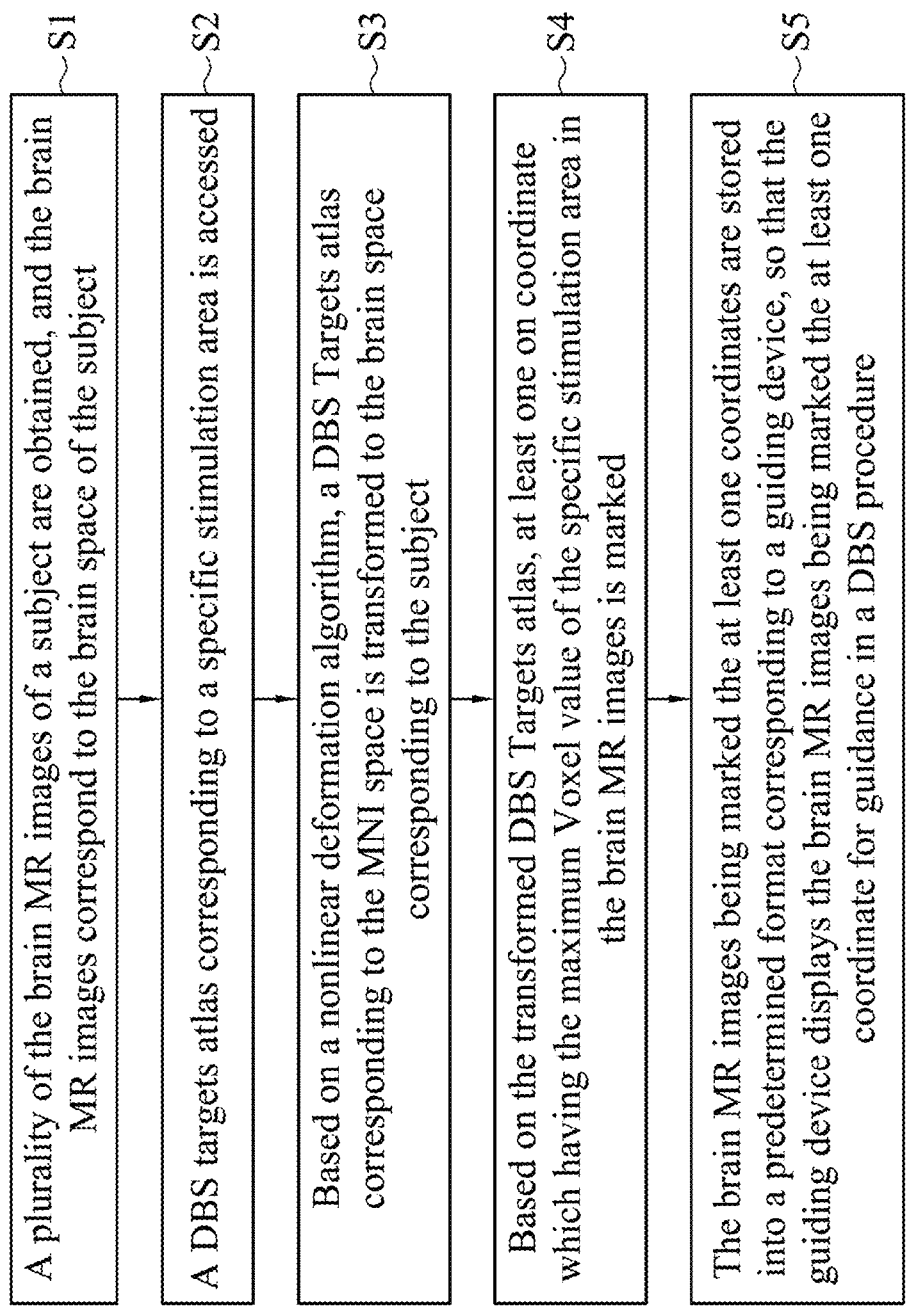
FIG. 2 schematically shows a flow diagram of a medical image making method according to some embodiments of the present disclosure.

FIG. 2 schematically shows a flow diagram of a medical image making method according to some embodiments of the present disclosure. As FIG. 2 shows, in some embodiments, the medical image making method can be implemented with the medical image making system 100 as FIG. 1 shows. In some embodiments, detailed steps regarding the medical image making method are explained in the following paragraphs.

Step S1: A plurality of the brain MR images of a subject are obtained, and the brain MR images correspond to the brain space of the subject.

In some embodiments, the MRI equipment 300 can scan a specific quantity of brains of subjects so as to generate the brain MR images corresponding to the subject. In some embodiments, the MRI equipment 300 can store the brain MR images. In some embodiments, the MRI equipment 300 can send the brain MR images to the database 200 such that the database 200 stores the brain MR images. In some embodiments, the aforementioned brain MR images are brain MR images with high resolution, whose format is a Digital Imaging and Communications in Medicine (DICOM) format.

It should be understood that the subjects may suffer from the following diseases or symptoms: Essential Tremor (ET), Parkinson's Disease (PD), Dystonia, Obsessive-Compulsive Disorder (OCD), Epilepsy, Alzheimer's Disease (AD), Treatment-Resistant Depression (MD), Tourette's Syndrome (TS) and Addiction (ADD). Corresponding to the diseases' or symptoms' process, the brain MR images D1 can be considerable different or various.

In some embodiments, the processor 112 can be selectively coupled to the database 200 or the MRI equipment 300. Therefore, the processor 112 can access the brain MR images of the subject from the database 200 or the MRI equipment 300.

In some embodiments, the brain MR images are presented as gray-scale images, and different gray-scale areas in the gray-scale images correspond to different tissues such as Gray Matter, White Matter, and Cerebrospinal Fluid. However, owing to different sections of the MRI, the images may change in sequential order.

Step S2: A DBS targets atlas corresponding to a specific stimulation area is accessed.

In some embodiments, the processor 112 can store at least one Deep Brain Stimulation (DBS), and the at least one DBS Targets Atlas includes a specific Stimulation Area. It should be noted that, in some embodiments, the at least one DBS Targets Atlas corresponds to a Montreal Neurological Institute Space (MNI space), the MNI is a normalized brain space that has been used by Montreal Neurological Institute. Relatively, the specific stimulation area in the DBS Targets Atlas is the specific brain area in the normalized brain space.

It should be understood that, in some embodiments, the at least one DBS Targets Atlas is a DBS Targets Atlas that was used by the digital researchers who published the science article named "Probabilistic conversion of neurosurgical DBS electrode coordinates into MNI space" in NeuroImage Vol. 150. The researchers named in NeuroImage include Andreas Horn, Andreas A. Kühn, Angela Merkl, Ludy Shih, Ron Alterman and Michael Fox.

Based on the aforementioned research named "Probabilistic conversion of neurosurgical DBS electrode coordinates into MNI space", applying DBS to multiple areas of the human brain can respectively give the following disease for help or effect: Essential Tremor, can stimulate the area of Ventral Intermediate Nucleus (VIM); Parkinson's Disease, can stimulate the area of Subthalamic Nucleus (STN);

Dystonia, can stimulate the area of Globus Pallidus Internus (GPi); Obsessive-Compulsive Disorder, can stimulate the area of Anterior Limb of the Internal Capsule (ALIC); Epilepsy can stimulate the area of anterior thalamic nucleus (ATN); Alzheimer's Disease can stimulate the area of FORNIX; Treatment-Resistant Depression, can stimulate the area of Subcallosal Cingulate (SCC); Tourette's Syndrome, can stimulate the area of Centromedian Nucleus (CM), Periventricularis (Pv) or Nucleus Ventro-Oralis Internus (VO); Addiction, can stimulate the area of Nucleus Accumbens (NAc). It should be understood that the aforementioned DBS application areas are based on the researches to generalize the examples of feasible areas, but the present disclosure is not limited thereto.

Step S3: Based on a nonlinear deformation algorithm, a DBS Targets atlas corresponding to the MNI space is transformed to the brain space corresponding to the subject.

In some embodiments, the processor 112 can normalize the DBS Targets atlas (including the specific stimulation area) based on a Diffeomorphic Anatomical Registration Through Exponential Lie (DARTEL) algorithm, so that the DBS Targets atlas can be transformed to the brain space of subjects from the MNI space. Namely, DARTEL can be used to transform the DBS Targets atlas and the specific stimulation area deforms in the DBS Targets atlas to the specific brain space corresponding to individual differences of the subjects (including the sizes and the shapes of the brain of the subject).

It should be understood that, the aforementioned nonlinear transform is used to map the normalized DBS Targets atlas to the brain MR images corresponding to the subjects. Therefore, the processor 112 can correctly mark the aforementioned specific stimulation area to the parts of brain of the subject. In other words, the aforementioned nonlinear transform is a transforming procedure of applying the DBS Targets atlas to the subject for adapting individual differences of the subjects.

Step S4: Based on the transformed DBS Targets atlas, at least one on coordinate which having the maximum Voxel value of the specific stimulation area in the brain MR images is marked.

In some embodiments, the processor 112 can transform the DBS Targets atlas corresponding to the MNI space to the brain space corresponding to the subject. Namely, the processor 112 can obtain the brain MR images of the subjects first in order to obtain the brain space of the subject.

Furthermore, the processor 112 can transform the DBS Targets atlas (including the specific stimulation area) to the sizes and the shapes of the brain space corresponding to the subject, so that the DBS Targets atlas corresponds to the brain space of the subject. Furthermore, based on the transformed DBS Targets atlas, the processor 112 can mark the location corresponding to the specific stimulation area in the brain MR images of the subjects.

Figure 3:
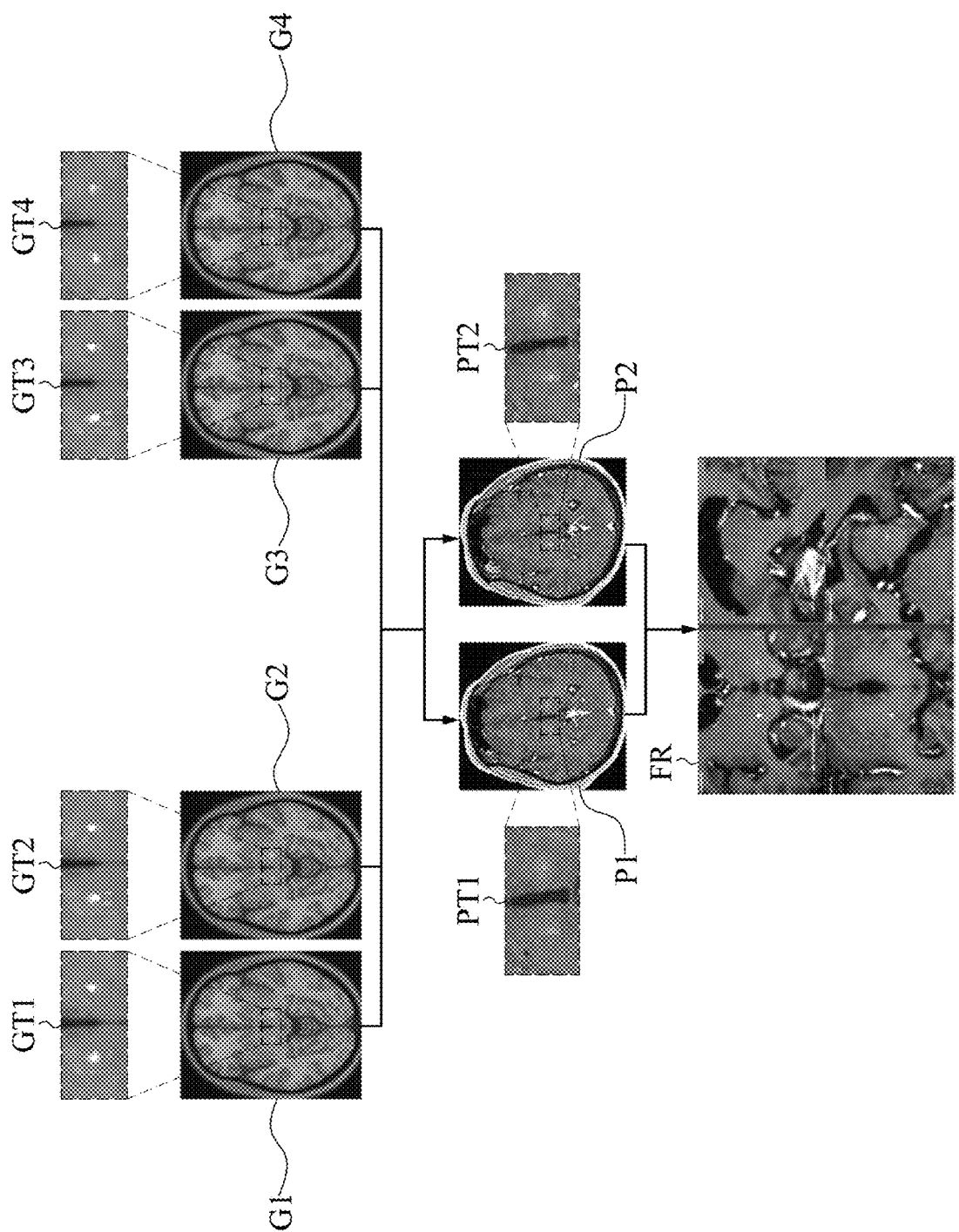
FIG. 3 schematically shows a schematic diagram of a medical image according to some embodiments of the present disclosure.

In order to facilitate the understanding of Step S3 and Step S4 of the disclosure, please refer to FIG. 3 together, which shows a schematic diagram of the medical images of some embodiments based on the disclosure.

In some embodiments, the processor 112 can capture the DBS Targets atlas corresponding to MNI Space, and the DBS Targets atlas can be at least the four DBS Targets atlas G1~G4 shown on the top row of FIG. 3. As FIG. 3 shows, each of the DBS Targets atlas G1~G4 corresponds to the drawing of partial enlargement GT1~GT4 respectively. In the drawing of partial enlargement GT1~GT4, it demonstrates that the subject has a white point at the left cerebral hemisphere and a white point at the right cerebral hemisphere, and the white points are the stimulated STN area of Parkinson's Disease in the aforementioned research named "Probabilistic conversion of neurosurgical DBS electrode coordinates into MNI space". The STN area is called Subthalamic Nucleus. There is a pair of the Subthalamic Nucleus which is located at the underside of the left cerebral hemisphere and the underside of the right cerebral hemisphere. Therefore, the two white points can be understood as STN stimulation area in the left cerebral hemisphere and the right cerebral hemisphere against Parkinson's Disease. It should be noted that, in the disclosure, the four DBS Targets atlas G1~G4 are corresponding to the same stimulation area. Since the MRI may correspond to the different sections of brain or different filming angles, the four DBS Targets atlas G1~G4, which correspond to the different sections of brain or different filming angles, may be used to describe the stimulation area in three-dimensional (or stereoscopical) manner.

Furthermore, the processor 112 can transform the DBS Targets atlas G1~G4 to the sizes and the shapes (these are obtained from the brain MR images of the subjects) of the brain space corresponding to the subject. As the second row shows in FIG. 3, the DBS Targets atlas G1~G4 are transformed to the transformed DBS Targets atlas P1~P2, and the specific stimulation areas in the drawing of partial enlargement GT1~GT4 are also transformed to the location of the brain space of the subject as shown in the drawing of partial enlargement PT1~PT2 in second row. The mapped brain MR images are demonstrated, white points are targeted at stimulation areas in the left cerebral hemisphere and the right cerebral hemisphere of the subject, which are the transformed specific stimulation area. The transformed DBS Targets atlas P1~P2 can be understood that it is a brain map which corresponds to the specific stimulation area and considers individual differences of the subject.

It should be understood that, in some embodiments, based on the transformed DBS Targets atlas P1~P2, the processor 112 can map on the brain MR images of the subject, and capture at least one coordinate corresponding to the brain MR images having the maximum (or called highest) Voxel value, and then mark the at least one coordinate in images. It should be understood that, in accordance with the aforementioned embodiments, the coordinate corresponding to brain MR images having the maximum Voxel value in the mapped brain MR images corresponds to the location of the specific stimulation area in the transformed DBS Targets atlas P1~P2 (it should be located at the two white points in the drawing of the partial enlargement PT1~PT2). Based on the DBS Targets atlas used in the aforementioned embodiments, the two white points are the stimulated STN area against Parkinson's disease on the research named "Probabilistic conversion of neurosurgical DBS electrode coordinates into MNI space".

Step S5: The brain MR images being marked the at least one coordinates are stored into a predetermined format corresponding to a guiding device, so that the guiding device displays the brain MR images being marked the at least one coordinate for guidance in a DBS procedure.

In some embodiments, the processor 112 can strengthen the marked brain MR images (including the coordinate of specific stimulation area) according to a maximum image intensity of the whole brain, and store the brain MR images being marked into a predetermined format that can be stored by the medical guiding device 400. For example, the predetermined format is a DICOM format. Therefore, the medical guiding device 400 can correctly load and display the brain MR images being marked for providing medical practitioners (i.e., doctors) watching the brain MR images being marked while the medical practitioners do the DBS surgery for the subject.

In some embodiments, medical guiding device 400 can display a guiding image FR in the bottom row of the FIG. 3 to provide the brain MR images being marked for the medical practitioners. The medical guiding device 400 displaying the guiding image FR can be understood as a guiding procedure of the DBS treatment against the subject. It should be understood that, the guiding image FR can demonstrate the coordinate corresponding to the labeled STN area in the drawing of the partial enlargement PT1~PT2 shown in FIG. 3, and the medical practitioners can insert a DBS Implantable Pulse Generator to the specific stimulation area of brain of the subject more accurately according to the coordinate, such that the stimulation locations of DBS is much more accurate.

According to aforementioned embodiments, the disclosure provides a medical image processing system and method, can mark specific stimulation areas based on DBS in the brain MR images, let the medical guiding device output the coordinate of the specific stimulation area corresponding to the brain of subject, be beneficial to confirm the specific stimulation area for medical practitioners, and then promote the treatment effect of DBS, substantially shorten the time of the surgery, and reduce complications caused by the electrical stimulation of the brain.

Furthermore, if the application in the field of surgical robotics, the medical image processing system and the method of the disclosure can bring the DBS into the field of semi-automatic surgery, wherein also a available implement of the disclosure.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A medical image processing system, comprising:
a memory, configured to store at least one instruction; and
a processor communicatively coupled to the memory, wherein the processor stores and executes the at least one instruction to:
obtain a plurality of brain Magnetic Resonance (MR) images corresponding to a subject, wherein the brain MR images correspond to a brain space of the subject;
access a deep brain stimulation (DBS) targets atlas corresponding to a specific stimulation area;
transform the DBS targets atlas from a Montreal Neurological Institute (MNI) brain space to the subject brain space based on Diffeomorphic Anatomical Registration Through Exponential Lie (DARTEL) algorithm;
mark at least one coordinate having a largest Voxel value in the specific stimulation area in the brain MR images basing on the DBS targets atlas being transformed; and
store the brain MR images being marked the at least one coordinate into a predetermined format corresponding to a guiding device, so that the guiding device displays the brain MR images being targeted with the at least one coordinate for guidance in a DBS procedure.

2. The medical image processing system of claim 1, wherein the specific stimulation area comprises a stimulation area in a left cerebral hemisphere and a stimulation area in a right cerebral hemisphere, and the processor captures the at least one coordinate having the largest Voxel value from the stimulation area in the left cerebral hemisphere and stimulation area in the right cerebral hemisphere respectively.

3. The medical image processing system of claim 1, wherein before the processor stores the brain MR images being marked the at least one coordinate into the predetermined format corresponding to the guiding device, the processor stores and executes the at least one instruction to strengthen marking the at least one coordinates in the brain MR images by a maximum of image intensity value of whole brain with image intensity value.

4. The medical image processing system of claim 1, wherein the predetermined format is a Digital Imaging and Communications in Medicine (DICOM) format.

5. The medical image processing system of claim 1, wherein a disease or a symptom to which the specific stimulation area corresponds comprises: Essential tremor, Parkinson's disease, Dystonia, Obsessive-compulsive disorder, Epilepsy, Alzheimer's disease, Treatment-resistant depression, Tourette's syndrome and Addiction.

6. A medical image making method, comprising:
obtaining a plurality of brain MR images corresponding to a subject, wherein the brain MR images correspond to a brain space of the subject;
accessing a DBS targets atlas corresponding to a specific stimulation area;
transforming the DBS targets atlas from a MNI brain space to the subject brain space based on DARTEL algorithm;
marking at least one coordinate having a largest Voxel value in the specific stimulation area in the brain MR images basing on the DBS targets atlas being transformed; and
storing the brain MR images being marked the at least one coordinates into a predetermined format corresponding to a guiding device, so that the guiding device displays the brain MR images being targeted with the at least one coordinate for guidance.

7. The medical image making method of claim 6, wherein the specific stimulation area comprises a stimulation area in a left cerebral hemisphere and a stimulation area in a right cerebral hemisphere, wherein marking at least one coordinate having the largest Voxel value in the specific stimulation area comprises capturing the at least one coordinate from the stimulation area in the left cerebral hemisphere and the stimulation area in the right cerebral hemisphere respectively.

8. The medical image making method of claim 6, wherein before storing the brain MR images being marked the at least one coordinate into the predetermined format corresponding to the guiding device, strengthening marking the at least one coordinates in the brain MR images by a maximum of image intensity value of whole brain with image intensity value.

9. The medical image making method of claim 6, wherein the predetermined format is a DICOM format.

10. The medical image making method of claim 6, wherein a disease or a symptom to which the specific stimulation area corresponds comprises: Essential tremor, Parkinson's disease, Dystonia, Obsessive-compulsive disorder, Epilepsy, Alzheimer's disease, Treatment-resistant depression, Tourette's syndrome and Addiction.

* * * * *